US011497442B1

(12) United States Patent
Schoess

(10) Patent No.: US 11,497,442 B1
(45) Date of Patent: Nov. 15, 2022

(54) EXERCISE EVALUATION AND RECOVERY THERAPY SYSTEM AND METHOD

(71) Applicant: EDEN MEDICAL, INC., Howard Lake, MN (US)

(72) Inventor: Jeffrey Norman Schoess, Howard Lake, MN (US)

(73) Assignee: EDEN MEDICAL, INC., Howard Lake, MN (US)

( * ) Notice: Subject to any disclaimer, the term of this patent is extended or adjusted under 35 U.S.C. 154(b) by 0 days.

(21) Appl. No.: 17/523,832

(22) Filed: Nov. 10, 2021

Related U.S. Application Data

(60) Provisional application No. 63/111,974, filed on Nov. 10, 2020.

(51) Int. Cl.
| | |
|---|---|
| *A61B 5/00* | (2006.01) |
| *A61B 5/1455* | (2006.01) |
| *G16H 40/67* | (2018.01) |
| *G16H 50/30* | (2018.01) |

(52) U.S. Cl.
CPC .......... *A61B 5/486* (2013.01); *A61B 5/0004* (2013.01); *A61B 5/14552* (2013.01); *G16H 40/67* (2018.01); *G16H 50/30* (2018.01)

(58) Field of Classification Search
None
See application file for complete search history.

(56) References Cited

U.S. PATENT DOCUMENTS

| | | | | |
|---|---|---|---|---|
| 2006/0063995 A1* | 3/2006 | Yodh | .................. | A61B 5/14551 600/323 |
| 2008/0097173 A1* | 4/2008 | Soyemi | .............. | A61B 5/14551 600/310 |
| 2008/0269574 A1* | 10/2008 | Mao | ....................... | A61B 5/145 600/309 |
| 2010/0292549 A1* | 11/2010 | Shuler | .................... | A61B 5/416 600/324 |
| 2013/0096403 A1* | 4/2013 | Dacso | ................ | A61B 5/14551 600/324 |
| 2013/0317367 A1* | 11/2013 | Shuler | .................. | A61B 5/0075 600/473 |

(Continued)

OTHER PUBLICATIONS

Garg, Parveen K., et al. "Physical activity during daily life and mortality in patients with peripheral arterial disease." Circulation 114.3 (2006): 242-248. (Year: 2006).*

(Continued)

*Primary Examiner* — Sean P Dougherty
*Assistant Examiner* — Benjamin S Melhus
(74) *Attorney, Agent, or Firm* — Underwood & Associates, LLC

(57) ABSTRACT

A method for assessing and reversing exercise impairment in adults having peripheral vascular disease includes quantifying a musculoskeletal deoxygenation level (MDL) of a human subject provided by a wearable near infrared spectroscopy system configured to measure the deoxygenation level during exercise, comparing the quantified MDL to a range of pre-determined healthy MDL values for the subject, and, if the quantified MDL is outside of the pre-determined target MDL values, determining a corrective exercise intensity level or 'dose' effective to bring the MDL of the subject within the target MDL values and reverse the exercise impairment.

18 Claims, 1 Drawing Sheet

(56) References Cited

U.S. PATENT DOCUMENTS

| | | | |
|---|---|---|---|
| 2016/0110513 A1* | 4/2016 | Tsai | G16Z 99/00 |
| | | | 706/52 |
| 2016/0151672 A1* | 6/2016 | Barnes | G06Q 30/02 |
| | | | 434/247 |
| 2016/0220808 A1* | 8/2016 | Hyde | A61B 5/6895 |
| 2017/0273609 A1* | 9/2017 | Gutwein | A61B 5/14552 |
| 2018/0249937 A1* | 9/2018 | Wiese | A61B 5/14552 |
| 2019/0159728 A1* | 5/2019 | Pritchard | A61F 5/0127 |
| 2021/0045671 A1* | 2/2021 | Wiese | A61B 5/0002 |
| 2021/0045686 A1* | 2/2021 | Wiese | A61B 5/14552 |
| 2021/0045687 A1* | 2/2021 | Wiese | A61B 5/14552 |

OTHER PUBLICATIONS

Garg, Parveen K., et al. "Physical activity during daily life and functional decline in peripheral arterial disease." Circulation 119.2 (2009): 251-260. (Year: 2009).*

* cited by examiner

US 11,497,442 B1

EXERCISE EVALUATION AND RECOVERY THERAPY SYSTEM AND METHOD

CROSS REFERENCE TO RELATED APPLICATIONS

This application claims priority to and the benefit under 35 USC § 119(e) of U.S. Provisional Patent Application No. 63/111,974 filed on Nov. 20, 2020 under the same application title, the contents of which are incorporated by reference in their entirety as if fully set forth herein.

STATEMENT REGARDING FEDERALLY SPONSORED RESEARCH OR DEVELOPMENT

This invention was made with government support under Project No. 1R43AG060868-01 awarded by the National Institute on Aging. The government has certain rights in the invention.

TECHNICAL FIELD

This disclosure relates to systems and methods for measuring and reversing exercise impairment of human subjects with peripheral vascular and arterial disease.

BACKGROUND

Peripheral arterial disease (PAD) is a prevalent, morbid, and mortal disease. In the US, the total economic impact of PAD in 2010 was $392 billion. The majority of the cost was for hospitalization costs at $344 billion (i.e. 88% of the total). In 2015, the economic burden of PAD exceeded that of diabetes, coronary artery disease and all cancers. The traditional risk factors for PAD include cigarette smoking, diabetes mellitus, hypertension, dyslipidaemia, and obesity. The risk of intermittent claudication is about twice as high in patients with diabetes as in individuals without diabetes. The risks of PAD increase with the severity of diabetes: for every 1% increase in hemoglobin A1c level, the risk of PAD increases by 26%. Better control of PAD can reduce cost, increase quality of life and decrease mortality rate.

The most common symptom of PAD is muscle pain in the lower limbs on exercise (intermittent claudication). Walking impairment occurs with fatigue, aching, cramping or pain in the buttock, thigh, calf or foot, particularly when symptoms are quickly relieved at rest. Pain comes on more rapidly when walking uphill than on the flat. Claudication can occur in both legs but is often worse in one leg. The potential biomechanical or biochemical mechanisms underlying the benefits of exercise therapy for PAD are exercise-induced angiogenesis, enhanced nitric oxide-dependent vasodilatation of the microcirculation, improved hemorheology, reduced vascular inflammation, improved glucose and fatty acid metabolism in skeletal muscle, improved muscle bioenergetics and oxidative stress, and improved peripheral nerve function.

The mechanisms underlying the response to exercise therapy include improvements in blood perfusion, muscle metabolism and mitochondrial function, peripheral nerve function, and walking efficiency. It is well established that exercise is effective for treating claudication among patients with PAD; however, many PAD patients avoid engaging in regular exercise because of fear-avoidance beliefs that exercise may worse their pain condition. This could be because of lack of a personalized tool allowing assessing/predicting patients' tolerance to perform exercise without overtaxing them.

Thus, a platform to fill this gap by providing an intuitive and objective metric predicting the tolerance of a PAD patients with intermittent claudication symptoms before reaching significant pain levels, as well as estimating the duration of needed rest before starting a new session of exercise, is an unmet need in the arts.

SUMMARY

In general, an exercise evaluation and recovery therapy system and method are disclosed. In an exemplary embodiment, a method for assessing and reversing exercise impairment in adults having peripheral vascular disease includes quantifying a musculoskeletal deoxygenation level (MDL) of a human subject provided by a wearable near infrared spectroscopy system configured to measure the deoxygenation level during exercise, comparing the quantified MDL to a range of pre-determined healthy MDL values for the subject, and, if the quantified MDL is outside of the pre-determined target MDL values, determining a corrective exercise intensity level or 'dose' effective to bring the MDL of the subject within the target MDL values and reverse the exercise impairment.

Unless otherwise defined, all technical and scientific terms used herein have the same meaning as commonly understood by one of ordinary skill in the art. Although methods and materials similar or equivalent to those described herein can be used in the practice or testing of any described embodiment, suitable methods and materials are described below. In addition, the materials, methods, and examples are illustrative only and not intended to be limiting. In case of conflict with terms used in the art, the present specification, including definitions, will control.

The foregoing summary is illustrative only and is not intended to be in any way limiting. In addition to the illustrative aspects, embodiments, and features described above, further aspects, embodiments, and features will become apparent by reference to the drawings and the following detailed description and claims.

DETAILED DESCRIPTION OF ILLUSTRATIVE EMBODIMENTS

Figure 1:
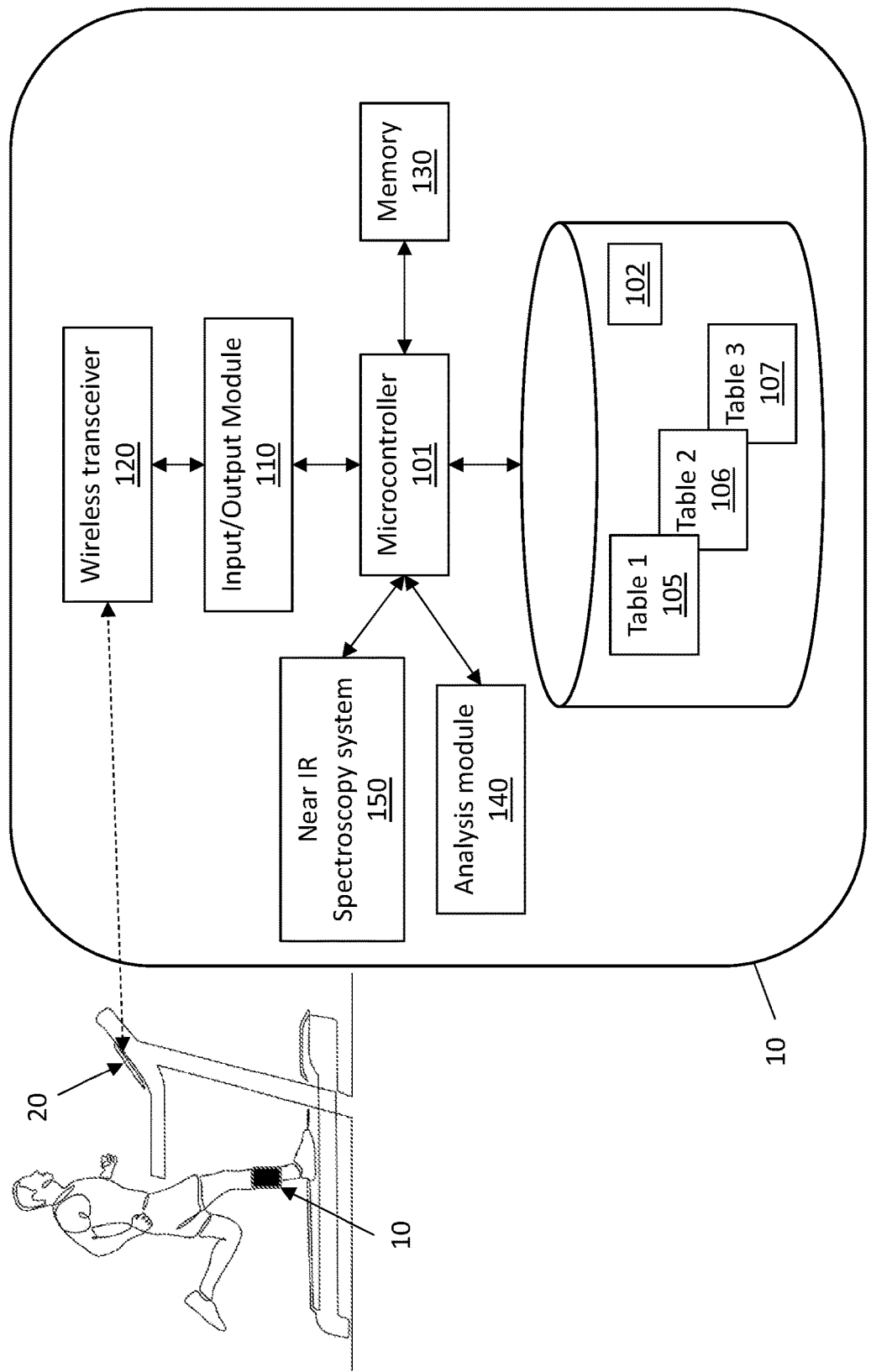
FIG. 1 is a system diagram of an exercise evaluation and recovery treatment system according to one embodiment.

It is well established that exercise is effective to treat claudication among patients with peripheral arterial disease (PAD); however, many PAD patients avoid engaging in regular exercise because of fear-avoidance beliefs that exercise may worse their pain condition. In general, an Exercise Evaluation and Recovery Treatment (hereinafter 'EXERT') platform is disclosed that can provide an intuitive and objective metric predicting the tolerance of PAD patients with intermittent claudication symptoms before experiencing significant pain. The EXERT platform can additionally estimate the duration of needed rest before starting a new session of exercise.

In one embodiment, an EXERT system is a mobile health (mHealth) solution for assessing exercise impairment of adult peripheral vascular disease (PVD) patients and increasing their exercise capacity. The public health problem of physical inactivity has proven resistant to research efforts aimed at elucidating its causes and personalized interventions designed to alter this cause. Most theoretical models of exercise behavior assume that the decision to engage in exercise is based on cognitive factors (e.g. weighting pros and cons).

Another, still under-appreciated possibility is that these decisions are influenced by affective variables, such as whether previous exercise experiences were associated with pleasure or displeasure. This is in particular true in older adults with peripheral arterial disease (PAD), in whom conventional exercise programs could easily overtax them and thus discourage them in engagement of future exercise. Overtaxing during exercise is believed to be highly dependent on muscle oxidative capacity and muscle deoxygenation. While this capacity could be improved by exercise intervention, it is essential to assess the capacity of the participant to avoid overtaxing and thus disengagement in continue exercise.

In this embodiment, the EXERT system includes a wearable Bluetooth enabled near infrared spectroscopy (NIRS) system to quantify skeletal muscle deoxygenation levels to assess muscle oxidative recovery between exercise sessions and avoid overtaxing participant during exercise. NIRS deoxygenation (Hb) provides a noninvasive measure of muscle oxygen extraction. The EXERT incorporates a recovery strategy to inform an exercise trainer on a capacity level of the patient and personalized exercise program to avoid overtaxing the patients and thus motivate them to engage in regular exercise to reverse the exercise impairment.

This is accomplished using an 'exercise prescription' or exercise 'dose' based on biofeedback intensity levels. The intensity level of exercise can be used as a prescription variable. The prescription could also include specific workloads (e.g., walking speed), duration and frequency of the exercise. The prescription dose could be adjusted remotely through a digital dashboard, as the therapist monitors patient performance (e.g., degree of claudication). Compliance, patient feedback and motivational incentives can be implemented via the digital dashboard.

In one embodiment, a method for assessing and reversing exercise impairment in adults having peripheral vascular disease includes quantifying a musculoskeletal deoxygenation level (MDL) of a human subject provided by a wearable near infrared spectroscopy system (NIRSS) configured to measure the deoxygenation level of the subject during exercise.

A suitable near infrared spectroscopy system can include, without limitation, a sensor board having an analog front end (AFE) integrated circuit (IC), inertial measurement unit (IMU), two near infrared LEDs and photodiodes. One suitable AFE IC is the Maxim 81641 Optical Unit provided by Maxim Integrated, San Jose, Calif., USA. The 81641 model features a two-channel data acquisition system, programmable LED driver (four full scale ranges, 32, 64, 93, and 124ma) to drive the two LEDs at 730 and 850 nm respectively, two optical readout channels (two photodiode interface), first-in-first out (FIFO) memory, two 19-bit A/Ds.

The MCU board can include the microcontroller IC to acquire the data, a wireless Bluetooth interface for user interface support, built-in read only (ROM) and random-access (RAM) memory and battery management. The optical channel has 4 full scale ranges. These ranges are 4 to 32 μA. It has dual LED drivers, two photodiodes to capture the near infrared light, and SPI bus interface.

In this embodiment, LED1 can be sampled first followed by LED 2, and then a direct ambient sample can be acquired as a baseline measurement for a $HbO_2/Hb$ algorithm calculation. The clock pulse width (tpw) is a minimum of 1.0 μs.

In this embodiment, the EXERT design includes an optical interface board (dual wavelength LEDs operable at 730 nm and 750 nm, respectively, 3 light pipes and 2 photodiodes mounted in a wearable package. The package design features a concave shape to fit and effectively project NIR light into the gastrocnemius muscle centered between medial/lateral heads.

In an alternative embodiment, two near infrared LEDs and one photodiode can be used which could be time multiplexed to capture the infrared light. The benefit of this layout would be the ability to select higher optical power LEDs to increase the depth of light penetration, projecting light into the deeper into the muscle to quantify deoxygenation.

The depth of light penetration can be chosen; one optimal depth is 10 mm. The path of light propagation follows the modified Beer-Lambert Law, an arcuate path depending on light attenuation due to absorption. The Beer-Lambert law defines the depth of penetration to be one-half the distance between the light source and photodetector, so a 10 mm depth defined the source-detector distance to be set at 20 mm.

Effective penetration of light can also determined by several other factors: wavelength, attenuation coefficient (scattering, refraction, and absorption), area of irradiance (power density–watts/$cm_2$), and light pulsing. The light pipe provides effective flux coupling projecting the light with minimum flux loss. The losses include LED insertion (Fresnel) loss (up to 4% loss) light leakage out the pipe wall (10 to 50% loss), and pipe exit Fresnel loss (4%). The radiation pattern at the pipe exit can be designed to maximize on-axis intensity and a narrow radiation pattern with a small viewing angle.

A dual wavelength, bi-color LED (Marubeni, part no. SMT 730/850D) for development can be utilized as it features peak wavelength operation at 730 and 850 nm. The LED has a wide radiation field of +/−62 degrees to provide the best flux capture. A PIN photodiode (Vishay Semi VEMD5060X01) can be used as a surface mount device with a 7.5 mm2 sensitive area with a high responsivity of 64 mV/(microwatt/cm2).

The LED projects light in the 12 mm acrylic light pipe and into the skin/tissue of the test subject. The light is absorbed, scattered and reflected back into a second light pipe, and detected by the photodiode. An LED operating at 124*ma* (310 mW) can project 1,150 mw/cm2 optical power output at the light pipe output. Taking in account the Fresnel losses, tissue loss due to scattering, reflection and absorption and light pipe return loss, the photodiode will detect 0.19 mw/cm2 of light energy.

In this embodiment, the method further includes comparing the quantified MDL to a range of pre-determined healthy MDL values for the subject. If the quantified MDL is outside of the pre-determined target MDL values, a corrective exercise intensity level can be determined that is effective to bring the MDL of the subject within the target MDL values and reverse the exercise impairment.

In this embodiment, the method can be applied to human subjects having a chronic disease such as peripheral vascular disease or peripheral arterial disease. A determination of the target MDL values can be customized based upon the chronic disease of the human subject.

Alternatively, the human subject may have a chronic disease, and a determination of the target MDL values can be customized based upon the chronic disease and one or more measured physiological factors of the human subject.

The wearable near infrared spectroscopy system can further include an electronic module configured to wirelessly transmit the measured deoxygenation level to a remote receiver during exercise. When those data are received and processed, a step in the present method can include instructing the human subject to increase or decrease an exercise intensity level if the quantified MDL value is outside of the pre-determined healthy MDL. Tables of MDL values for healthy subjects and those with particular chronic diseases may be kept, for example, in an electronic database for reference. Each chronic disease may be associated with a particular table of MDL data.

In one embodiment, the method further includes instructing the human subject to change to a different exercise if the quantified MDL value is outside of the pre-determined healthy MDL range. This can be accomplished, for example and without limitation, by a trainer, a physical therapist, an occupational therapist, a personal electronic device such as a smart phone, tablet or other known electronic device.

In one embodiment, determining a corrective exercise intensity level includes determining a modified exercise workload, duration, frequency or a combination thereof. This information can then be relayed to the subject.

In one embodiment, the wearable near infrared spectroscopy system includes an infrared light source and a detector configured to receive the infrared light source after propagating through a selected portion of the human subject's skin tissue. Non-limiting examples of preferred skin tissue includes the calf muscle, wrist or forearm.

In one embodiment, the near infrared spectroscopy system can include one or more physiological sensors, such as, but without limitation, a deoxygenation probe, an accelerometer, a pulse or pulse-less oximeter, a pulse-rate monitor, a moisture sensor, a thermometer or a combination thereof.

In a general aspect, a system for assessing and reversing exercise impairment of a human subject with adult peripheral vascular disease is disclosed. In one embodiment, the system for assessing exercise impairment includes a wearable device. The wearable device can include at least one sensor configured to measure a musculoskeletal deoxygenation level (MDL) in the human subject while exercising. For example, a sensor of the type described herein can be placed on a selected portion of tissue of the subject, such as the exterior portion of a calf muscle, wrist or forearm. The system further includes a memory configured to store a plurality of the musculoskeletal deoxygenation levels in a digital-electronic format, such as in electronic tabular form or in a relational database. The system further includes an input/output module configured for transmitting the collected musculoskeletal deoxygenation levels to a remote electronic device.

The input/output module can be, for example, a wireless transmitter utilizing, for example, Bluetooth or WiFi communication protocols. The system further includes a reference table of target musculoskeletal deoxygenation levels stored in digital-electronic format, such as in electronic tabular form or in a relational database, for example. The system further includes a processor in signal communication with the reference table, the processor being configured to compare at least one of the plurality of the musculoskeletal deoxygenation levels to the reference table. The system further includes a software module configured to determine a corrective exercise intensity level effective to bring the MDL of the subject within a target musculoskeletal deoxygenation level values while the human subject is exercising and reverse the exercise impairment In one embodiment, the input/output module includes a wireless transmitter and receiver.

In this embodiment, the sensor is a near infrared spectroscopy system as described herein. The wearable device can further include one or more physiological sensors in addition to the near infrared spectroscopy system. The one or more physiological sensors can be for example, and without limitation, an accelerometer, an oximeter, a pulse-rate monitor, a moisture sensor, a thermometer or a combination thereof.

In this embodiment, the reference table of target musculoskeletal deoxygenation levels comprises musculoskeletal deoxygenation levels representative of a healthy human subject. The reference table of target musculoskeletal deoxygenation levels can include musculoskeletal deoxygenation levels representative of a human subject having a chronic illness, such as peripheral vascular disease or peripheral arterial disease.

A number of illustrative embodiments have been described. Nevertheless, it will be understood that various modifications may be made without departing from the spirit and scope of the various embodiments presented herein. Accordingly, other embodiments are within the scope of the following claims.

We claim:

1. A method for assessing and reversing exercise impairment in adults having peripheral vascular disease, comprising:
    quantifying a musculoskeletal deoxygenation level (MDL) of a human subject provided by a wearable near infrared spectroscopy system configured to measure said deoxygenation level during exercise;
    comparing said quantified MDL to a range of pre-determined healthy MDL values for said subject; and
    if said quantified MDL is outside of said range of pre-determined healthy MDL values:
        determining a corrective exercise intensity level effective to bring said MDL of said subject within said range of pre-determined healthy MDL values and reverse said exercise impairment; and
        instructing said human subject to increase or decrease an exercise intensity level:
    wherein said human subject has a chronic disease, and wherein a determination of said range of pre-determined healthy MDL values are customized based upon said chronic disease of said human subject.

2. The method of claim 1, wherein said chronic disease is peripheral vascular disease.

3. The method of claim 1, wherein said chronic disease is peripheral arterial disease.

4. The method of claim 1, wherein said human subject has a chronic disease, and wherein a determination of said range of pre-determined healthy MDL values are customized based upon said chronic disease and one or more measured physiological factors of said human subject.

5. The method of claim 1, wherein said wearable near infrared spectroscopy system comprises an electronic module configured to wirelessly transmit said measured deoxygenation level to a remote receiver during exercise.

6. The method of claim 1, wherein said determining a corrective exercise intensity level comprises determining a modified exercise workload, duration, frequency or a combination thereof.

7. The method of claim 1, wherein said wearable near infrared spectroscopy system comprises an infrared light source and a detector configured to receive said infrared light source after propagating through a selected portion of said human subject's skin tissue.

8. The method of claim 1, wherein said near infrared spectroscopy system comprises one or more physiological sensors.

9. The method of claim 8, wherein said one or more physiological sensors is a deoxygenation probe, an accelerometer, an oximeter, a pulse-rate monitor, a moisture sensor, a thermometer or a combination thereof.

10. A method for assessing and reversing exercise impairment in adults having peripheral vascular disease, comprising:
   quantifying a musculoskeletal deoxygenation level (MDL) of a human subject provided by a wearable near infrared spectroscopy system configured to measure said deoxygenation level during exercise;
   comparing said quantified MDL to a range of pre-determined healthy MDL values for said subject; and
   if said quantified MDL is outside of said range of pre-determined healthy MDL values:
      determining a corrective exercise intensity level effective to bring said MDL of said subject within said range of pre-determined healthy MDL values and reverse said exercise impairment; and
      instructing said human subject to change to a different exercise if said quantified MDL value is outside of said range of pre-determined healthy MDL values;
   wherein said human subject has a chronic disease, and wherein a determination of said range of pre-determined healthy MDL values are customized based upon said chronic disease of said human subject.

11. The method of claim 10, wherein said chronic disease is peripheral vascular disease.

12. The method of claim 10, wherein said chronic disease is peripheral arterial disease.

13. The method of claim 10, wherein said human subject has a chronic disease, and wherein a determination of said range of pre-determined healthy MDL values are customized based upon said chronic disease and one or more measured physiological factors of said human subject.

14. The method of claim 10, wherein said wearable near infrared spectroscopy system comprises an electronic module configured to wirelessly transmit said measured deoxygenation level to a remote receiver during exercise.

15. The method of claim 10, wherein said determining a corrective exercise intensity level comprises determining a modified exercise workload, duration, frequency or a combination thereof.

16. The method of claim 10, wherein said wearable near infrared spectroscopy system comprises an infrared light source and a detector configured to receive said infrared light source after propagating through a selected portion of said human subject's skin tissue.

17. The method of claim 10, wherein said near infrared spectroscopy system comprises one or more physiological sensors.

18. The method of claim 17, wherein said one or more physiological sensors is a deoxygenation probe, an accelerometer, an oximeter, a pulse-rate monitor, a moisture sensor, a thermometer or a combination thereof.

* * * * *